(12) United States Patent
Barbu et al.

(10) Patent No.: US 8,396,533 B2
(45) Date of Patent: Mar. 12, 2013

(54) METHOD AND SYSTEM FOR CATHETER DETECTION AND TRACKING IN A FLUOROSCOPIC IMAGE SEQUENCE

(75) Inventors: Adrian Barbu, Tallahassee, FL (US); Wei Zhang, Plainsboro, NJ (US); Norbert Strobel, Heroldsbach (DE); Adam K. Galant, Carpentersville, IL (US); Ulrich Bill, Effeltrich (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1110 days.

(21) Appl. No.: 12/221,732

(22) Filed: Aug. 6, 2008

(65) Prior Publication Data
US 2009/0062641 A1  Mar. 5, 2009

Related U.S. Application Data

(60) Provisional application No. 60/956,988, filed on Aug. 21, 2007.

(51) Int. Cl.
*A61B 5/05* (2006.01)
(52) U.S. Cl. .......................... 600/427; 600/424; 382/154
(58) Field of Classification Search .................. 600/317, 600/321, 329, 407, 411, 427, 434, 435, 438, 600/424; 606/27, 28, 41, 45; 382/128, 130, 382/154, 160
See application file for complete search history.

(56) References Cited

U.S. PATENT DOCUMENTS

| | | | |
|---|---|---|---|
| 6,304,776 B1 | 10/2001 | Muntermann | |
| 6,370,421 B1 | 4/2002 | Williams et al. | |
| 6,780,182 B2 | 8/2004 | Bowman et al. | |
| 7,016,521 B1* | 3/2006 | Florent | 382/128 |
| 2002/0118874 A1* | 8/2002 | Chung et al. | 382/154 |
| 2003/0169847 A1* | 9/2003 | Karellas et al. | 378/98.3 |
| 2006/0058633 A1* | 3/2006 | Hoshino et al. | 600/410 |
| 2006/0079761 A1* | 4/2006 | Tu et al. | 600/425 |
| 2006/0182224 A1 | 8/2006 | Besson | |
| 2006/0182225 A1 | 8/2006 | Besson | |
| 2006/0247521 A1* | 11/2006 | McGee | 600/434 |
| 2006/0257006 A1* | 11/2006 | Bredno et al. | 382/128 |
| 2007/0073135 A1* | 3/2007 | Lee et al. | 600/407 |
| 2007/0270692 A1* | 11/2007 | Barbu et al. | 600/431 |
| 2007/0299425 A1 | 12/2007 | Waner et al. | |
| 2008/0039715 A1 | 2/2008 | Wilson et al. | |
| 2008/0108901 A1 | 5/2008 | Baba et al. | |

OTHER PUBLICATIONS

Zhuowen Tu, Probabilistic Boosting Tree: Learning Discriminative Models for Classification, recognition and Clusting, IEEE International Conference on Computer Vision, Oct. 2005, vol. 2, pp. 1589-1596.*

* cited by examiner

*Primary Examiner* — James Kish
*Assistant Examiner* — Michael N Fisher

(57) ABSTRACT

A method and system for detecting and tracking an ablation catheter tip in a fluoroscopic image sequence is disclosed. Catheter tip candidates are detected in each frame of the fluoroscopic image sequence using marginal space learning. The detected catheter tip candidates are then tracked over all the frames of the fluoroscopic image sequence in order to determine an ablation catheter tip location in each frame.

25 Claims, 5 Drawing Sheets

METHOD AND SYSTEM FOR CATHETER DETECTION AND TRACKING IN A FLUOROSCOPIC IMAGE SEQUENCE

This application claims the benefit of U.S. Provisional Application No. 60/956,988, filed Aug. 21, 2007, the disclosure of which is herein incorporated by reference.

BACKGROUND OF THE INVENTION

The present invention relates to fluoroscopic imaging of the heart, and more particularly to detecting and tracking an ablation catheter tip in fluoroscopic image sequences of the heart.

Cardiac arrhythmia is an abnormality of the electrical rhythm of the heart. Cardiac arrhythmia is often treated using radiofrequency ablation to modify the electrical pathways of the heart. In order to construct an electrical map of the heart, different catheters are inserted into the arteries and guided to the heart. Based on such an electrical map, doctors attempt to identify locations of abnormal electrical activity in the heart. An ablation catheter with a special tip is used to perform the ablation by applying energy (radiofrequency) at the locations of abnormal electrical activity. This destroys, or ablates, the tissue at these locations and interrupts the triggers for the heart arrhythmia.

The entire ablation operation is monitored with real-time fluoroscopic images. Fluoroscopic images are X-ray images taken over a period of time resulting in an image sequence. It is desirable to detect and track the ablation catheter tip in such a fluoroscopic image sequence.

BRIEF SUMMARY OF THE INVENTION

The present invention provides a method and system for detecting and tracking an ablation catheter tip in fluoroscopic image sequences of the heart. Such detection and tracking of an ablation catheter tip can be used to obtain a 3D reconstruction of the ablation catheter tip location from a bi-plane fluoro resulting from two fluoroscopic image sequences of an ablation procedure obtained from different angles. The 3D reconstruction of the ablation catheter tip location can be used in conjunction with a CT volume of a patient to provide real-time 3D navigation capabilities inside the heart.

In one embodiment of the present invention, a fluoroscopic image sequence of the heart is received. Catheter tip candidates are detected in each frame of the fluoroscopic image sequence using marginal space learning. The catheter tip candidates can be detected by detecting position in a first marginal space learning level and detecting position and orientation in a second marginal space learning level. The number of catheter tip candidates resulting from the marginal space learning detection can be reduced using non-maximal suppression. The catheter tip candidates are then tracked over all the frames of the fluoroscopic image sequence in order to determine an ablation catheter tip location in each frame. The catheter tip candidates can be tracked by determining a trajectory between the catheter tip candidates over all the frames that has a minimal trajectory cost.

These and other advantages of the invention will be apparent to those of ordinary skill in the art by reference to the following detailed description and the accompanying drawings.

DETAILED DESCRIPTION

The present invention is directed to a method and system for detecting and tracking an ablation catheter tip in fluoroscopic image sequences of the heart. Embodiments of the present invention are described herein to give a visual understanding of the ablation catheter tip detection and tracking method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
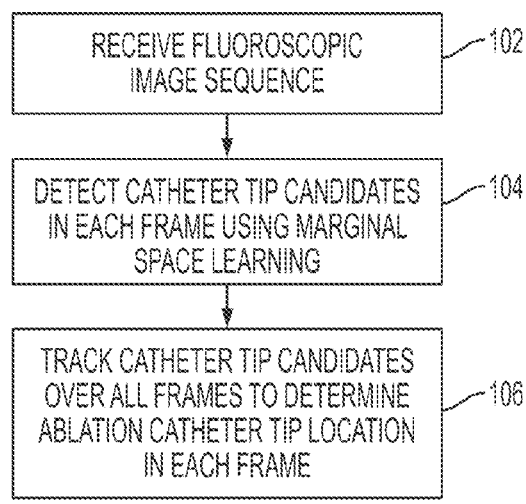
FIG. 1 illustrates a method for detecting and tracking an ablation catheter tip in a fluoroscopic image sequence according to an embodiment of the present invention.

FIG. 1 illustrates a method for detecting and tracking an ablation catheter tip in a fluoroscopic image sequence according to an embodiment of the present invention. At step 102, a sequence of fluoroscopic images is received. The sequence of fluoroscopic images can be X-ray images of the heart taken at a regular interval over a time frame while monitoring an ablation procedure. Each image in the sequence can be referred to as a frame. The sequence of fluoroscopic images can be received directly from an X-ray imaging device or can be loaded, for example from a memory or storage of a computer system, or some other computer readable medium.

At step 104, catheter tip candidates are detected in each frame of the fluoroscopic image sequence using marginal space learning. Marginal space learning is a learning technique, in which the dimensionality of the search space is gradually increased. The learning and searching computations are performed in a sequence of marginal spaces that are selected such that the marginal probabilities have small entropies. A classifier is trained at each marginal space learning level to detect candidates based on the search space at each level.

Figure 2:
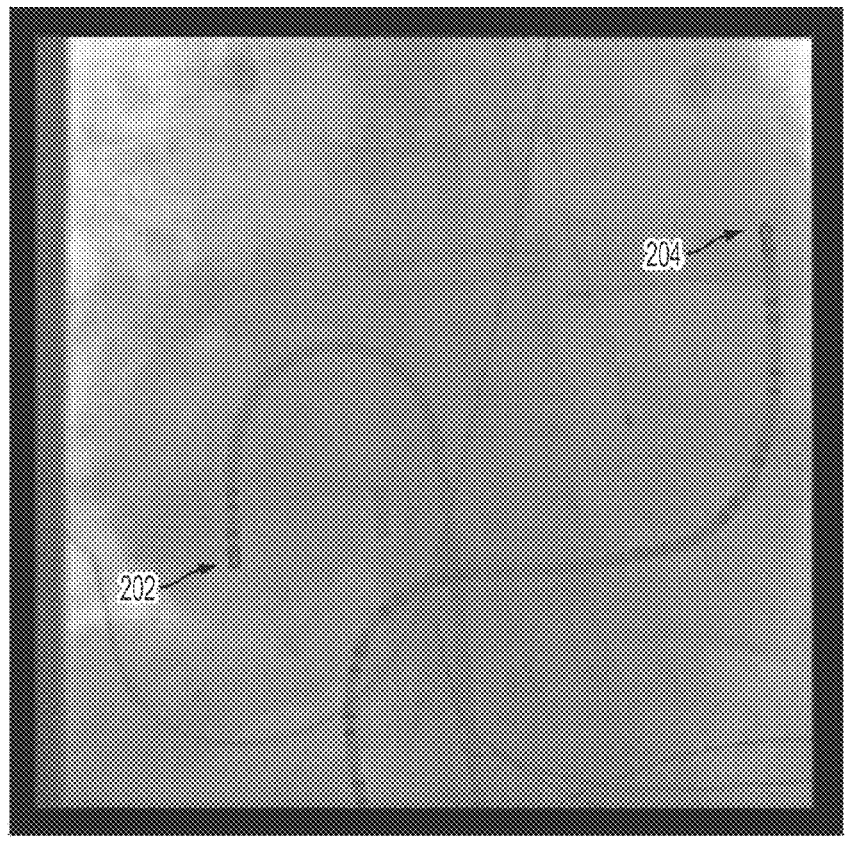
FIG. 2 illustrates an exemplary training image with annotated catheter tips.

The catheter tip has three parameters: the position (x, y) and the orientation θ. Two levels of marginal space learning can be used to determine candidate parameters for catheter tips in each frame. In the first level, a classifier is trained to detect candidates based on position. In the second level, a classifier is trained to detect candidates based on position and orientation. Each classifier at each level can be trained using a Probabilistic Boosting Tree (PBT) based on training data. The training data is fluoroscopic images with ground truth catheter tips annotated therein. Since the appearance of an ablation catheter tip is similar to the appearance of other types of catheter tips in a fluoroscopic image, other catheter tips in addition to ablation catheter tips can be annotated as positive in the training images. FIG. 2 illustrates an exemplary training image with annotated catheter tips 202 and 204. As illustrated in FIG. 2, catheter tip 202 is an ablation catheter tip and catheter tip 204 is another type of catheter tip.

At each marginal space learning level, a PBT classifier is trained by recursively constructing a tree, where each of the nodes represents a strong classifier. Once the strong classifier of each node is trained, the input training data for the node is classified into two sets (positives and negatives) using the learned strong classifier. The two new sets are fed to left and right child nodes respectively to train the left and right child nodes. In this way, the Probabilistic Boosting Tree will be constructed recursively. The PBT is advantageous for the tip detection, since during the training it can cluster the appearance of the catheter tip in different classes, which can be a useful way of dealing with multiple catheter types.

Figure 3:
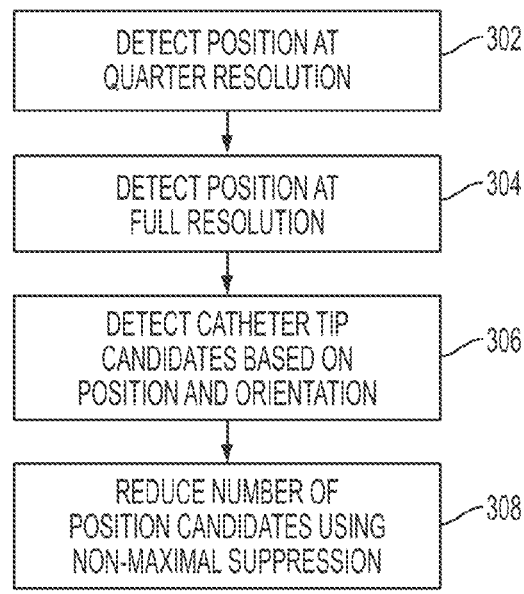
FIG. 3 illustrates a method of detecting catheter tip candidates in a fluoroscopic image using marginal space learning according to an embodiment of the present invention.

Once the PBT classifiers are trained for each level, the classifiers can be used to detect catheter tip candidates in input fluoroscopic images. Catheter tip candidates are detected by sequentially detecting candidates using the classifier trained for each marginal space learning level. FIG. 3 illustrates a method of detecting catheter tip candidates in a fluoroscopic image using marginal space learning according to an embodiment of the present invention. The method of FIG. 3 can be repeated for each frame of the received fluoroscopic image sequence.

At step 302, catheter tip positions are detected at quarter (25%) resolution using a first classifier. Starting at quarter resolution allows the detection process to start with a smaller search space to quickly determine areas where catheter tip candidates are likely present. The integral image of the quarter resolution fluoroscopic image and Haar features can be used to train a three level PBT classifier to detect the quarter resolution catheter tip positions. Based on the PBT probability, the best position (x, y) candidates above a threshold are kept for further processing. For example, the best 500 quarter resolution position candidates may be kept.

At step 304, catheter tip positions are detected at full resolution using a second classifier. At this level, the integral image and Haar features on the full resolution fluoroscopic images can be used to train a three level PBT to detect the position candidates. For training, the best position candidates from the quarter resolution level are rescaled and perturbed to generate the training samples for this level. For position detection, the best position candidates detected by the first classifier are rescaled to generate possible position candidates to be processed by the second classifier. Since the first classifier detects position candidates at quarter resolution, each candidate kept from the first classifier generates four possible candidates to be processed by the second classifier. Based on the PBT probability resulting from the second classifier, the best position (x, y) candidates above a threshold are kept for further processing. For example, the best 500 full resolution position candidates may be kept.

At step 306, catheter tip candidates are detected based on position and orientation using a third classifier. For this level, steerable features based on image intensity and some steerable filter responses can be used to train a PBT classifier to detect candidates based on position and orientation. This PBT classifier can have four levels, with the first level enforced as a cascade. Each of the position candidates (x, y) from the previous level is augmented with an angle θ having any of 60 discrete values. Thus, for each position candidate (x, y) kept from the second classifier, 60 catheter tip candidates (x, y, θ) are generated to be processed by the third classifier. Based on the PBT probability resulting from the third classifier, the best catheter tip candidates (x, y, θ) above a threshold are selected to be further processed using non-maximal suppression. For example, the best 500 catheter tip candidates may be selected.

At step 308, non-maximal suppression is used to reduce the number of catheter tip candidates. Non-maximal suppression reduces the number of tip candidates by discarding candidates in a neighborhood of other better candidates. First, the catheter tip candidate having the highest probability (PBT probability resulting from the third classifier) is selected. Then, any catheter tip candidates in a neighborhood (e.g., within n pixels) of the selected candidate are discarded. For example, any candidates within two or three pixels of the selected candidate may be discarded. These steps are repeated until each catheter tip candidate has either been selected or discarded. This results in a set of catheter tip candidates for each frame or fluoroscopic image.

Figure 4:
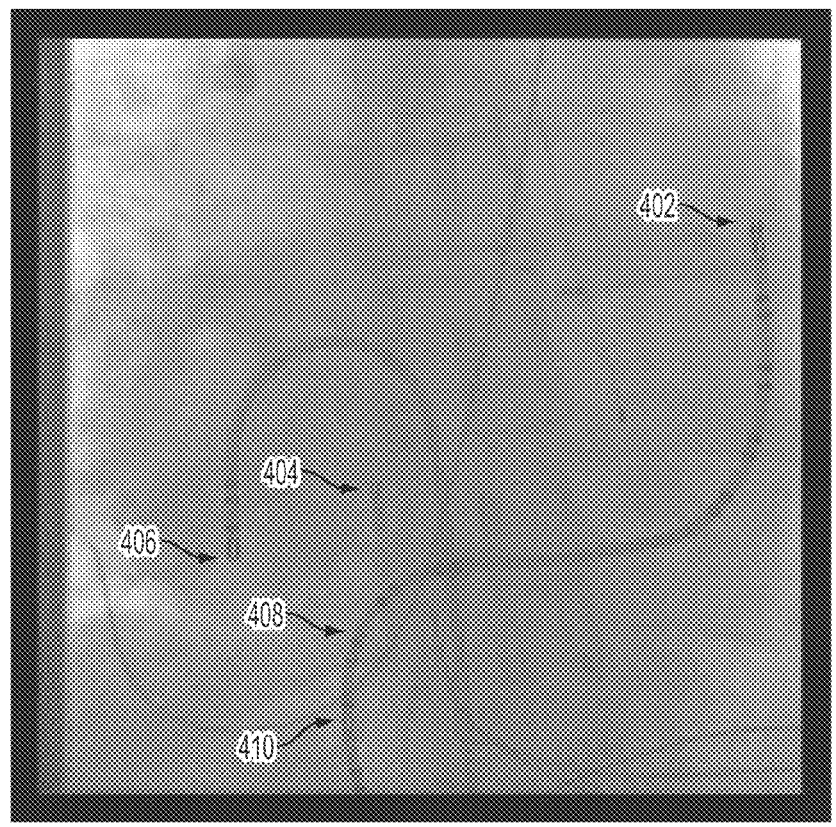
FIG. 4 illustrates catheter tip candidates detected using the method of FIG. 3 in an exemplary fluoroscopic image.

FIG. 4 illustrates catheter tip candidates detected using the method of FIG. 3 in an exemplary fluoroscopic image. As illustrated in FIG. 4, catheter tip candidates 402, 404, 406, 408, and 410 are detected as the most probable catheter tip locations and orientations using method of FIG. 3.

Returning to FIG. 1, at step 106, the catheter tip candidates are tracked over all of the frames in the fluoroscopic image sequence to determine an ablation catheter tip location in each frame. Without any tracking, the most probable catheter tip candidate in any frame may not be close to the true ablation catheter tip. This is due to perturbation of the ablation catheter tip by motion blur or by occlusion. Moreover, it is desirable that nothing is detected in a frame when the ablation catheter tip is not present in that frame. Accordingly, the catheter tip candidates are tracked through the frames of the fluoroscopic image sequence in order to determine the most probable tip trajectory, which gives the location of the ablation catheter tip in each frame.

As described above, a small set of catheter tip candidates results from the catheter tip detection using marginal space learning. In order to obtain the best tip trajectory over the sequence of frames, a variant of the well known Viterbi algorithm can be used. Let $s_1^t=(x_1^t, y_1^t, \theta_1^t), s_2^t, \ldots, s_{k_t}^t$ be the catheter tip candidates detected for frame t. For $dt=1, \ldots, 9$, a motion probability is calculated using two-dimensional histograms $h^{pos}$ and $h^{neg}$. For each pair of locations $(s^t, s^{t+dt})$, the bin $(d, a)=(\ln|(x^t, y^t)-(x^{t+dt}, y^{t+dt})|, \theta^t-\theta^{t+dt})$ is calculated. If both locations are close to the same tip trajectory, the bin (d, a) of histogram $h^{pos}$ is incremented, and if the locations are not close to the same tip trajectory, the bin (d, a) of histogram $h^{neg}$ is incremented. Accordingly, histograms $h^{pos}$ and $h^{neg}$ are generated having bins corresponding to each possible catheter tip candidate pair between catheter tip candidates on different frames in the fluoroscopic image sequence. The probability for each bin (each catheter tip candidate pair) can then be calculated as $$P(s^t, s^{t+dt}) = P(d,a) = h^{pos}(d,a)/(h^{pos}(d,a) + h^{neg}(d,a)).$$

A continuation cost $C(s^t, s^{t+dt})$, reflecting a cost of catheter tip candidate $s^t$ in frame t moving to catheter tip candidate $s^{t+dt}$ in frame t+dt, can then be generated based on the probability $P(s^t, s^{t+dt})$, such that $C(s^t, s^{t+dt}) = -\ln(P(s^t, s^{t+dt})/(1-P(s^t, s^{t+dt})))$. Based the continuation cost, a trajectory cost of a tip trajectory from each catheter tip candidate s in each frame t, can be defined as:

$$C(s) = -\sum_{t=0}^{n} \ln \frac{P(s^t)}{1-P(s^t)} - \sum_{dt=1}^{4} \sum_{t=0}^{n-dt} \ln \frac{P(s^t, s^{t+dt})}{1-P(s^t, s^{t+dt})}.$$

Figure 5:
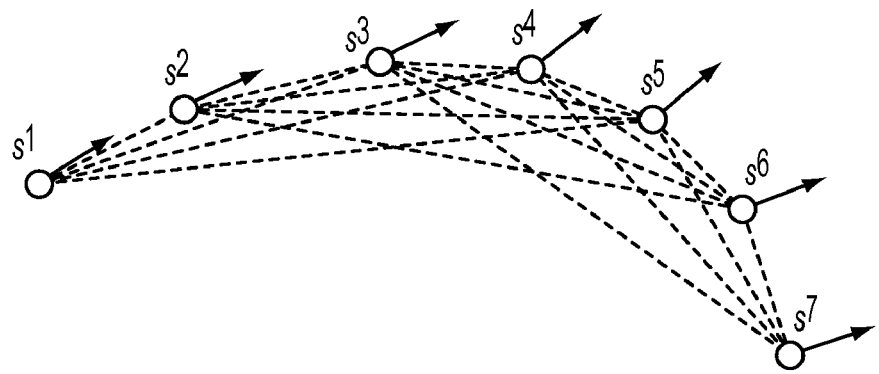
FIG. 5 illustrates calculation of trajectory costs from catheter tip candidates based on continuation probabilities.

FIG. 5 illustrates calculation of trajectory costs from catheter tip candidates based on continuation probabilities. As illustrated in FIG. 5 and expressed in the above equation, the trajectory cost from each catheter tip candidate $s^1$-$s^7$ is calculated based on continuation probabilities between the catheter tip candidate and catheter tip candidates along the trajectory in the next four frames (unless the last frame is reached). For example, the trajectory cost from candidate $s^1$ is based on the continuation probability between $s^1$ and $s^2$, the continuation probability between $s^1$ and $s^3$, the continuation probability between $s^1$ and $s^4$, and the continuation probability between $s^1$ and $s^5$.

Figure 6:
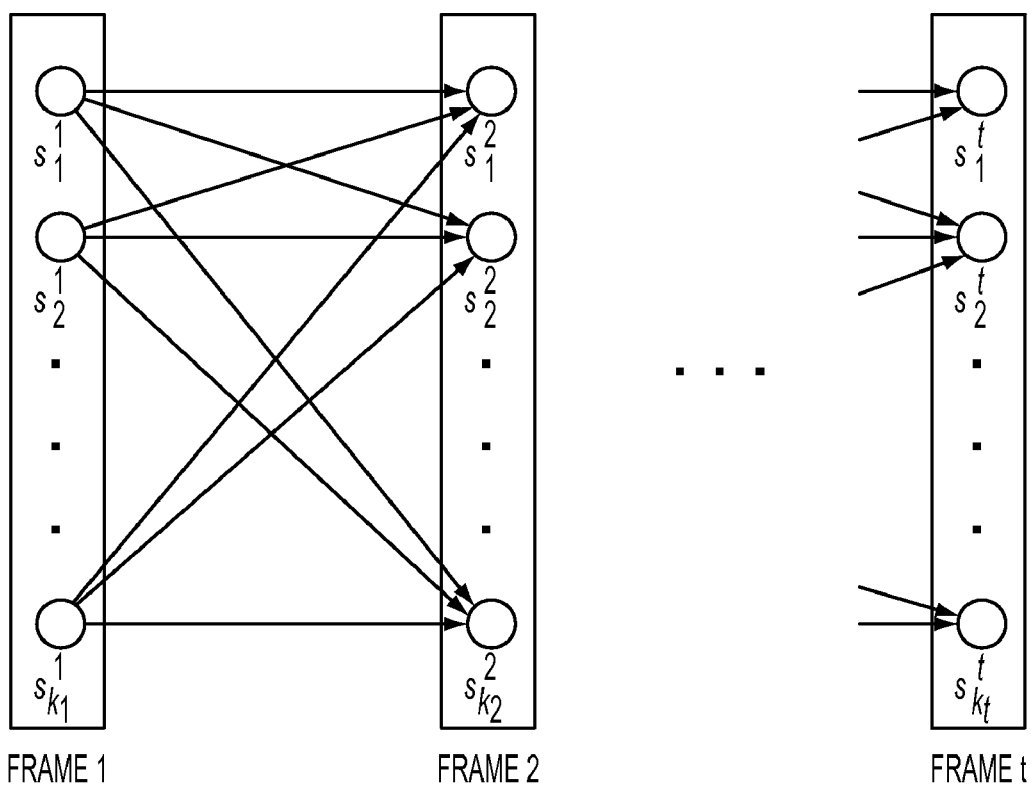
FIG. 6 illustrates determining a trajectory having a minimal cost over the frames of an image sequence.

In order to determine the ablation catheter tip location in each frame, the tip trajectory with the lowest trajectory cost is determined. The trajectory with the minimal cost can be inferred using a variant of the well-known Viterbi algorithm. FIG. 6 illustrates determining the trajectory having the minimal cost through the frames of an image sequence. As illustrated in FIG. 6, at each frame t, the trajectory cost of the best trajectory ending in each candidate $s_k^t$ is determined using the following recurrence formula:

$$C_k^t = -\ln \frac{P(s_k^t)}{1 - P(s_k^t)} + \min_i \left( C_i^{t-1} - \ln \frac{P(s_i^{t-1}, s_k^t)}{1 - P(s_i^{t-1}, s_k^t)} \right).$$

At each frame, the location of the catheter tip candidate from the trajectory with the lowest cost is selected, if the trajectory cost is less than the smallest cost from the previous frame. If the trajectory cost is not lower than the smallest cost from the previous frame, it means that the continuity cost from the previous frame to the current frame is high, and no good trajectory exists from the previous frame to the current frame. Therefore, the current frame will not show any ablation catheter detection.

The selected catheter tip candidate in each frame is the location (position and orientation) of the ablation catheter tip in that frame. It is possible to then output the ablation catheter tip locations by displaying the ablation catheter tip locations in the frames of the fluoroscopic image sequence. These ablation catheter tip locations can also be stored or used in additional medical imaging procedures. For example, the above described method can be performed for two fluoroscopic image sequences taken simultaneously from different angles while monitoring an ablation procedure. The ablation catheter tip locations for the frames of the two sequences can then be used to generate a 3D reconstruction of the ablation tip location. This 3D reconstruction in conjunction with a previously acquired CT volume can provide real-time navigation capabilities inside the heart.

Figure 7:
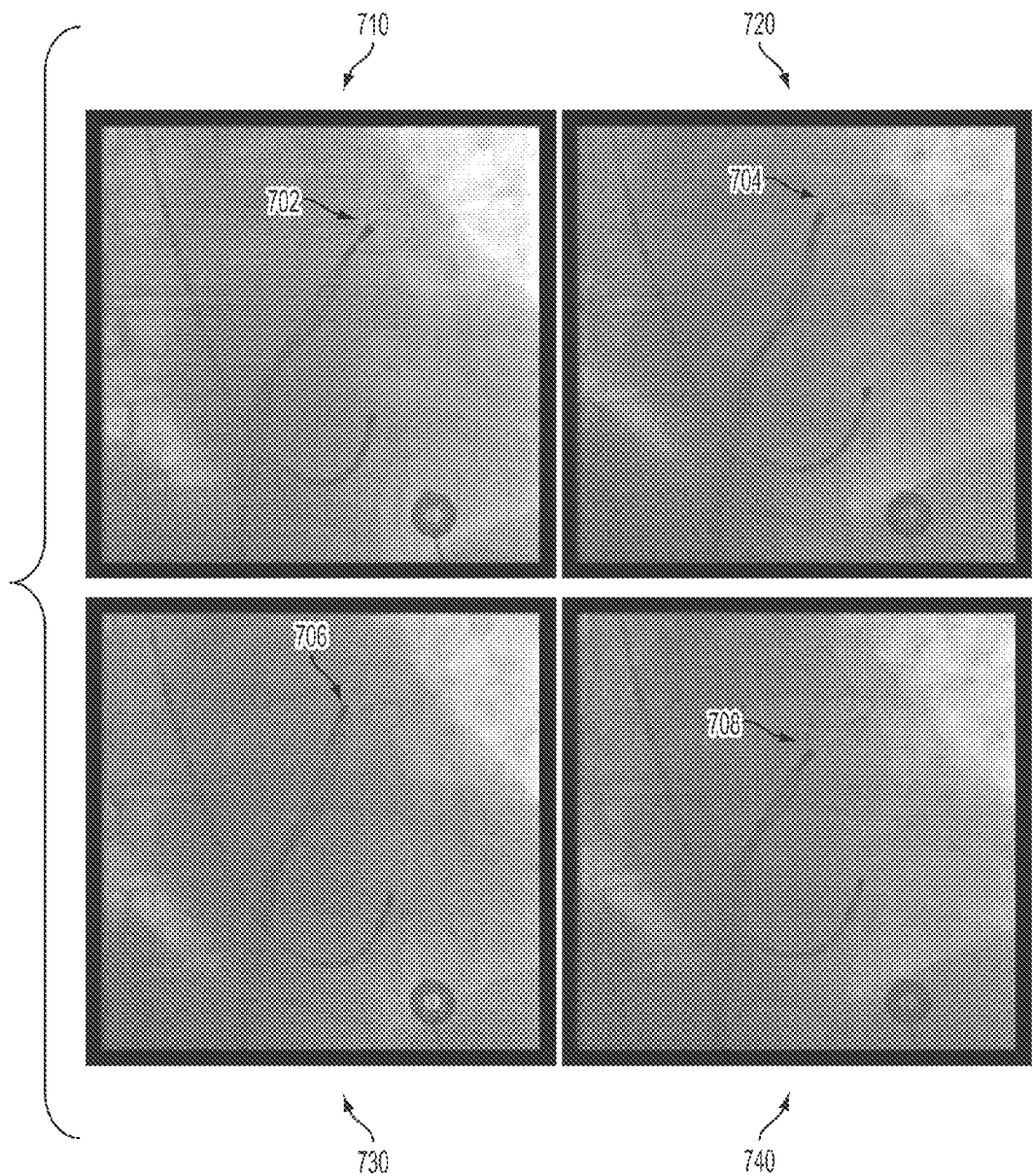
FIG. 7 illustrates exemplary ablation catheter tip detection results.

FIG. 7 illustrates exemplary ablation catheter tip detection results. As illustrated in FIG. 7, the ablation catheter tips 702, 704, 706, and 708 are detected in frames, 710, 720, 730, and 740, respectively, using the method of FIG. 1.

Figure 8:
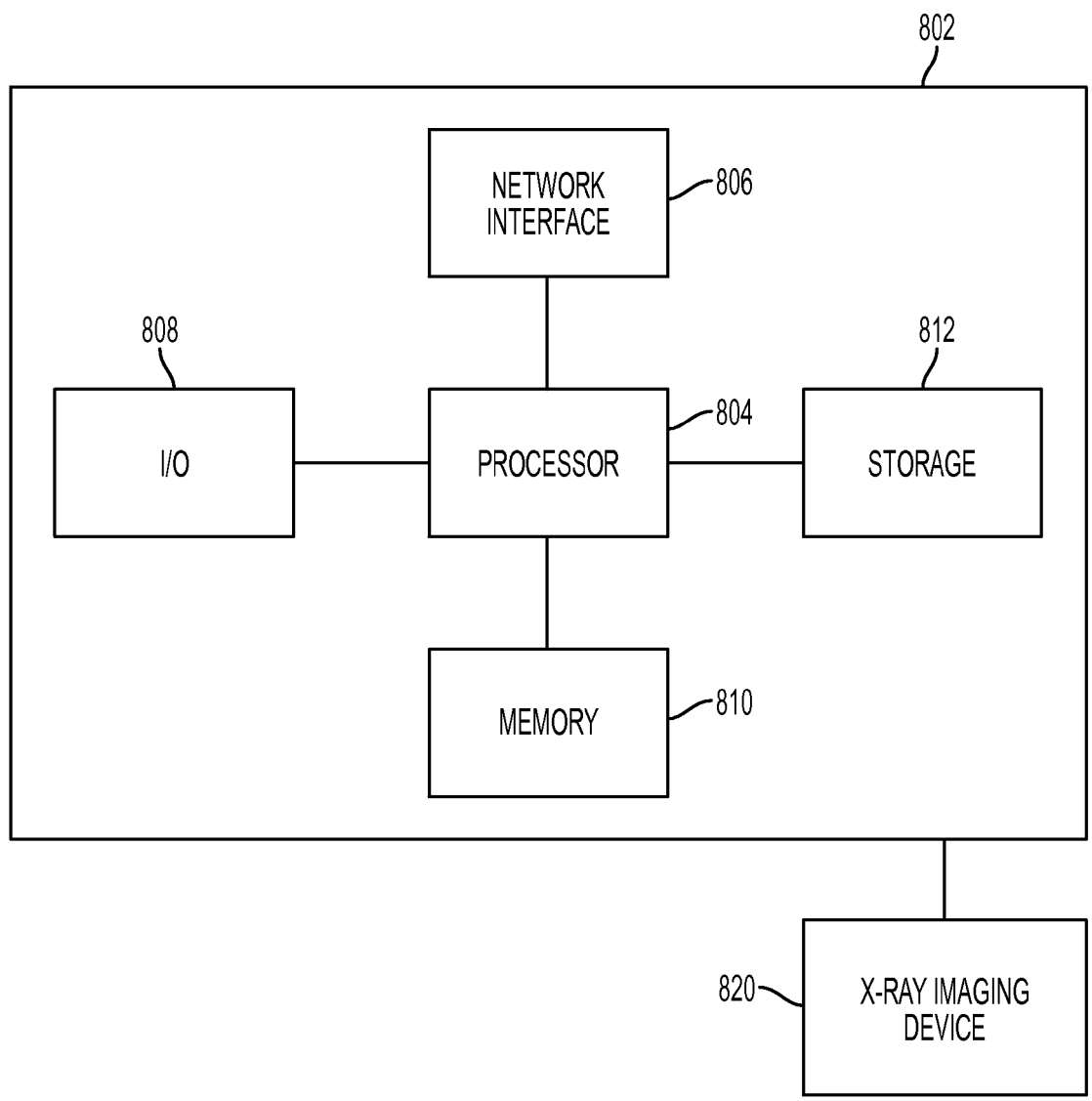
FIG. 8 is a high level block diagram of a computer capable of implementing the present invention.

The above-described methods for ablation catheter tip detection and tracking can be implemented on a computer using well-known computer processors, memory units, storage devices, computer software, and other components. A high level block diagram of such a computer is illustrated in FIG. 8. Computer 802 contains a processor 804 which controls the overall operation of the computer 802 by executing computer program instructions which define such operation. The computer program instructions may be stored in a storage device 812, or other computer readable medium (e.g., magnetic disk, CD ROM, etc.), and loaded into memory 810 when execution of the computer program instructions is desired. Thus, the method steps of FIGS. 1 and 3 can be defined by the computer program instructions stored in the memory 810 and/or storage 812 and controlled by the processor 804 executing the computer program instructions. An X-ray imaging device 820 can be connected to the computer 802 to input X-ray radiographs to the computer 802. It is possible to implement the X-ray imaging device 820 and the computer 802 as one device. It is also possible that the X-ray imaging device 820 and the computer 802 communicate wirelessly through a network. The computer 802 also includes one or more network interfaces 806 for communicating with other devices via a network. The computer 802 also includes input/output devices 808 that enable user interaction with the computer 802 (e.g., display, keyboard, mouse, speakers, buttons, etc.) One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for detecting and tracking an ablation catheter tip in a fluoroscopic image sequence including a plurality of frames, comprising:
    detecting catheter tip candidates in each frame of the fluoroscopic image sequence using marginal space learning, wherein the marginal space learning detects the catheter tip candidates in a series of marginal space learning levels of increasing dimensionality; and
    tracking the catheter tip candidates over all of the frames of the fluoroscopic image sequence to determine an ablation catheter tip location in each frame of the fluoroscopic image sequence.

2. The method of claim 1, wherein said step of detecting tip candidates in each frame of the fluoroscopic image sequence comprises, for each frame:
    detecting positions of catheter tip candidates in the frame in a first marginal space learning level; and
    detecting catheter tip candidates including position and orientation in the frame in a second marginal space learning level.

3. The method of claim 2, wherein said step of detecting positions of catheter tip candidates is performed by a first classifier trained using a Probabilistic Boosting Tree (PBT), and said step of detecting catheter tip candidates including position and orientation is performed by a second classifier trained using a PBT.

4. The method of claim 2, wherein said step of detecting tip candidates in each frame of the fluoroscopic image sequence further comprises, for each frame:
    reducing a number of catheter tip candidates using non-maximal suppression.

5. The method of claim 4, wherein said step of reducing a number of catheter tip candidates using non-maximal suppression comprises:

selecting a catheter tip candidate with a highest probability;

discarding catheter tip candidates in a neighborhood of the selected catheter tip candidate; and repeating said selecting and discarding steps until each catheter tip candidate has been selected or discarded.

6. The method of claim 1, wherein said step of detecting tip candidates in each frame of the fluoroscopic image sequence comprises, for each frame:

detecting a number of position candidates at quarter resolution using a first classifier;

scaling said position candidates at quarter resolution to generate a plurality of full resolution potential position candidates;

detecting a number of position candidates at full resolution from said full resolution potential position candidates using a second classifier;

augmenting each of said position candidates at full resolution using a plurality of discrete angles to generate a plurality of potential position and orientation candidates;

detecting a number of catheter tip candidates from said potential position and orientation candidates using a third classifier; and reducing the number of catheter tip candidates using non-maximal suppression.

7. The method of claim 6, wherein said first, second, and third classifiers are Probabilistic Boosting Tree (PBT) classifiers.

8. The method of claim 1, wherein said step of tracking the catheter tip candidates over all of the frames of the fluoroscopic image sequence to determine an ablation catheter tip location in each frame of the fluoroscopic image sequence comprises:

determining a trajectory between catheter tip candidates over all of the frames in the fluoroscopic image sequence having a minimal cost; and selecting a catheter tip candidate in each frame in the trajectory having the minimal cost as the ablation catheter tip location for that frame.

9. The method of claim 8, wherein said step of determining a trajectory between catheter tip candidates over all of the frames in the fluoroscopic image sequence having a minimal cost comprises at each frame:

calculating a best trajectory ending at each catheter tip candidate in that frame;

determining a catheter tip candidate that has the best trajectory with a lowest cost; and if the lowest cost is less than a lowest cost determined at a previous frame, selecting the catheter tip candidate as the ablation catheter tip location for the frame.

10. An apparatus for detecting and tracking an ablation catheter tip in a fluoroscopic image sequence including a plurality of frames, comprising:

means for detecting catheter tip candidates in each frame of the fluoroscopic image sequence using marginal space learning, wherein the marginal space learning detects the catheter tip candidates in a series of marginal space learning levels of increasing dimensionality; and means for tracking the catheter tip candidates over all of the frames of the fluoroscopic image sequence to determine an ablation catheter tip location in each frame of the fluoroscopic image sequence.

11. The apparatus of claim 10, wherein said means for detecting tip candidates in each frame of the fluoroscopic image sequence comprises:

means for detecting positions of catheter tip candidates in each frame in a first marginal space learning level; and means for detecting catheter tip candidates including position and orientation in each frame in a second marginal space learning level.

12. The apparatus of claim 11, further comprising:

means for training a first classifier using a Probabilistic Boosting Tree (PBT) corresponding to said first marginal space learning level; and means for training a second classifier using a PBT corresponding to said second marginal space learning level.

13. The apparatus of claim 11, wherein said means for detecting tip candidates in each frame of the fluoroscopic image sequence further comprises:

means for reducing a number of catheter tip candidates detected in each frame using non-maximal suppression.

14. The apparatus of claim 10, wherein said means for detecting tip candidates in each frame of the fluoroscopic image sequence comprises, for each frame:

means for detecting a number of position candidates at quarter resolution using a first classifier;

means for scaling said position candidates at quarter resolution to generate a plurality of full resolution potential position candidates;

means for detecting a number of position candidates at full resolution from said full resolution potential position candidates using a second classifier;

means for augmenting each of said position candidates at full resolution using a plurality of discrete angles to generate a plurality of potential position and orientation candidates;

means for detecting a number of catheter tip candidates from said potential position and orientation candidates using a third classifier; and means for reducing the number of catheter tip candidates using non-maximal suppression.

15. The apparatus of claim 14, wherein said first, second, and third classifiers are Probabilistic Boosting Tree (PBT) classifiers.

16. The apparatus of claim 10, wherein said means for tracking the catheter tip candidates over all of the frames of the fluoroscopic image sequence to determine an ablation catheter tip location in each frame of the fluoroscopic image sequence comprises:

means for determining a trajectory between catheter tip candidates over all of the frames in the fluoroscopic image sequence having a minimal cost; and means for selecting a catheter tip candidate in each frame in the trajectory having the minimal cost as the ablation catheter tip location for that frame.

17. The apparatus of claim 16, wherein said means for determining a trajectory between catheter tip candidates over all of the frames in the fluoroscopic image sequence having a minimal cost comprises:

means for calculating a best trajectory ending at each catheter tip candidate in each frame;

means for determining a catheter tip candidate in each frame that has the best trajectory with a lowest cost; and means for selecting the catheter tip candidate as the ablation catheter tip location for a frame if the lowest cost is less than a lowest cost determined at a previous frame.

18. A non-transitory computer readable medium encoded with computer program instructions for detecting and tracking an ablation catheter tip in a fluoroscopic image sequence including a plurality of frames, the computer program instructions defining steps comprising:

detecting catheter tip candidates in each frame of the fluoroscopic image sequence using marginal space learning, wherein the marginal space learning detects the catheter tip candidates in a series of marginal space learning levels of increasing dimensionality; and tracking the catheter tip candidates over all of the frames of the fluoroscopic image sequence to determine an ablation catheter tip location in each frame of the fluoroscopic image sequence.

19. The non-transitory computer readable medium of claim 18, wherein the computer program instructions defining the step of detecting tip candidates in each frame of the fluoroscopic image sequence comprise computer program instructions defining the following steps for each frame:

detecting positions of catheter tip candidates in the frame in a first marginal space learning level; and detecting catheter tip candidates including position and orientation in the frame in a second marginal space learning level.

20. The non-transitory computer readable medium of claim 19, wherein the computer program instructions defining the step of detecting tip candidates in each frame of the fluoroscopic image sequence further comprise computer program instructions defining the following step for each frame:

reducing a number of catheter tip candidates using non-maximal suppression.

21. The non-transitory computer readable medium of claim 20, wherein the computer program instructions defining the step of reducing a number of catheter tip candidates using non-maximal suppression comprise computer program instructions defining the following steps:

selecting a catheter tip candidate with a highest probability;

discarding catheter tip candidates in a neighborhood of the selected catheter tip candidate; and repeating said selecting and discarding steps until each catheter tip candidate has been selected or discarded.

22. The non-transitory computer readable medium of claim 18, wherein the computer program instructions defining the step of detecting tip candidates in each frame of the fluoroscopic image sequence comprise computer program instructions defining the following steps for each frame:

detecting a number of position candidates at quarter resolution using a first classifier;

scaling said position candidates at quarter resolution to generate a plurality of full resolution potential position candidates;

detecting a number of position candidates at full resolution from said full resolution potential position candidates using a second classifier;

augmenting each of said position candidates at full resolution using a plurality of discrete angles to generate a plurality of potential position and orientation candidates;

detecting a number of catheter tip candidates from said potential position and orientation candidates using a third classifier; and reducing the number of catheter tip candidates using non-maximal suppression.

23. The non-transitory computer readable medium of claim 22, wherein said first, second, and third classifiers are Probabilistic Boosting Tree (PBT) classifiers.

24. The non-transitory computer readable medium of claim 18, wherein the computer program instructions defining the step of tracking the catheter tip candidates over all of the frames of the fluoroscopic image sequence to determine an ablation catheter tip location in each frame of the fluoroscopic image sequence comprise computer program instructions defining the following steps:

determining a trajectory between catheter tip candidates over all of the frames in the fluoroscopic image sequence having a minimal cost; and selecting a catheter tip candidate in each frame in the trajectory having the minimal cost as the ablation catheter tip location for that frame.

25. The non-transitory computer readable medium of claim 24, wherein the computer program instructions defining the step of determining a trajectory between catheter tip candidates over all of the frames in the fluoroscopic image sequence having a minimal cost comprise computer program instructions defining the following steps for each frame:

calculating a best trajectory ending at each catheter tip candidate in that frame;

determining a catheter tip candidate that has the best trajectory with a lowest cost; and if the lowest cost is less than a lowest cost determined at a previous frame, selecting the catheter tip candidate as the ablation catheter tip location for the frame.

* * * * *